US009107601B2

(12) United States Patent
Schmidt et al.

(10) Patent No.: US 9,107,601 B2
(45) Date of Patent: Aug. 18, 2015

(54) METHOD FOR DETERMINING ELECTRICAL CONDUCTION PATH INFORMATION IN A CHAMBER WALL OF A VENTRICLE

(71) Applicants: Markus Schmidt, Nuremberg (DE); Sebastian Schmidt, Weisendorf (DE)

(72) Inventors: Markus Schmidt, Nuremberg (DE); Sebastian Schmidt, Weisendorf (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 160 days.

(21) Appl. No.: 13/759,529

(22) Filed: Feb. 5, 2013

(65) Prior Publication Data

US 2013/0204116 A1 Aug. 8, 2013

(30) Foreign Application Priority Data

Feb. 8, 2012 (DE) .......................... 10 2012 201 832

(51) Int. Cl.
*A61B 5/055* (2006.01)
*G01R 33/44* (2006.01)
*G01R 33/56* (2006.01)
*A61B 5/05* (2006.01)

(52) U.S. Cl.
CPC .............. *A61B 5/055* (2013.01); *G01R 33/443* (2013.01); *G01R 33/5608* (2013.01)

(58) Field of Classification Search
CPC .......................... G01R 33/443; G01R 33/5608
USPC ....................................................... 600/410
See application file for complete search history.

(56) References Cited

U.S. PATENT DOCUMENTS

| 6,205,349 | B1 | 3/2001 | Bundy |
| 7,604,721 | B2* | 10/2009 | Groll et al. ............... 204/403.01 |
| 2008/0077032 | A1 | 3/2008 | Costa |
| 2010/0160765 | A1 | 6/2010 | Badger |
| 2010/0160768 | A1 | 6/2010 | Badger |
| 2015/0025364 | A1* | 1/2015 | Groth et al. ................... 600/424 |

OTHER PUBLICATIONS

YingLi Lu et al., "Segmentation of Left Ventricle in Cardiac Cine MRI: An Automated Image-Driven Method," Functional Imaging and Modeling of the Heart 2009, LNCS 5528, pp. 339-347 (2009).*
Qing Lou et al., "Quantitative Panoramic Imaging of Epicardial Electrical Activity," Annals of Biomedical Engineering, vol. 36, No. 10, pp. 1649-1658 (2008).*

(Continued)

*Primary Examiner* — Long V Le
*Assistant Examiner* — Katherine McDonald

(57) ABSTRACT

A method for determining electrical conduction path information in a chamber wall of a ventricle of a patient is provided. A three-dimensional magnetic resonance image data set is recorded showing the ventricles using a recording technology which allows an assignment of an electrical conductivity to a voxel based on the magnetic resonance image dataset. The chamber wall is segmented in the magnetic resonance image dataset. Conductivity determined from the image data is assigned to sub-regions of the chamber wall corresponding to individual voxels of the magnetic resonance image dataset. A model of the chamber wall is created as a function of the conductivities and segmentation. A conduction path information item is determined describing an electrical conduction path running from a start point to a destination point through the chamber wall in the model.

13 Claims, 3 Drawing Sheets

(56) References Cited

OTHER PUBLICATIONS

Troy J. Badger et al., "MRI in cardiac electrophysiology: the emerging role of delayed enhancement MRI in atrial fibrillation ablation," Future Cardiology, vol. 5, No. 1, pp. 1-8 (2009).*

Mithun Prasad et al., "Automated quantification of 3D regional myocardial wall thickening from gated Magnetic Resonance images," J Magn Reson Imaging, vol. 31. No. 10, pp. 317-327, (2010).*

Suk Hoon Oh et al., "Conductivity and current density image reconstruction using harmonic Bz algorithm in magnetic resonance electrical impedance tomography," Physics in Medicine and Biology, Issue 48, pp. 3101-3116 (2003).*

Peters et al: "Detection of Pulmonary Vein and Left Atrial Scar after Catheter Ablation with Three-dimensional Navigator-gated Delayed Enhancement MR Imaging: Initial Experience"; Radiology, vol. 243; 3, pp. 690-695; Jun. 2007; Others; 2007;.

Dössel, O et al: "A Framework for Personalization of Computational Models of the Human Atria"; In: Annual International Conference of the IEEE EMBS, 2011, p. 4324-4328.; Others; 2011;.

* cited by examiner

METHOD FOR DETERMINING ELECTRICAL CONDUCTION PATH INFORMATION IN A CHAMBER WALL OF A VENTRICLE

CROSS REFERENCE TO RELATED APPLICATIONS

This application claims priority of German application No. 10 2012 201 832.8 filed Feb. 8, 2012, which is incorporated by reference herein in its entirety.

FIELD OF INVENTION

The application relates to a method for determining electrical conduction path information in a chamber wall of a ventricle, such as of an atrium, of a patient. The application also relates to a magnetic resonance facility.

BACKGROUND OF INVENTION

Different diseases are known, in which the normal operation of the heart is disrupted by aberrant conduction paths in ventricles, such as the atrium, which can cause serious physical problems.

One of the best known of these diseases is atrial fibrillation, which affects several million people per year at least temporarily in the US alone. The aberrant conduction paths mentioned above occur in the atria of the heart so that electrical signals, which control the musculature of the atria, circulate and for example stimulate the muscles at such a high frequency that the regular pumping activity of the atrium no longer takes place.

This means that the pumping activity of the heart is generally reduced without the atrial contribution. Also the blood flow in the atria decreases, so that blood clots can form, which are then transported in the circulation through the body. Finally it is possible for the heart rate to increase, when electrical signals are conducted to the heart at too high a frequency. Arrhythmias can then result.

The reason for the occurrence of aberrant conduction paths in the atrium or in the right or left ventricle is frequently damage to the inner walls of the chambers, for example due to ischemia or inflammation. The damaged tissue has different electrical properties and conducts the electrical signals more effectively. Of significance is the formation of so-called reentry circuits, in which the stimulus circulates, and ectopic foci, which generate pulses at high frequency outside the normal stimulus formation system (sinus node, AF node, etc.). Ectopic foci are generally located in the region where the pulmonary veins open into the atrium.

In order to treat such diseases, such as atrial fibrillation, it has been proposed that the aberrant conduction paths should be interrupted by ablation and the ectopic foci should be isolated. A high-frequency catheter for example can be used for this purpose, being positioned on the inside of the chamber wall and modifying this by specific application of an alternating current, so that electrical conductivity is reduced. An attempt is hereby made to isolate the openings of the pulmonary veins specifically from the remainder of the atrium. The problem arises here of assessing whether the treatment was successful or how likely it is that atrial fibrillation will recur. Diagnostic questions are also relevant, when for example methods are sought for determining the course of conduction paths.

To assess a therapeutic treatment of atrial fibrillation, it was proposed in the article "Detection of Pulmonary Vein and Left Atrial Scar after Catheter Ablation with Three-dimensional Navigator-gated Delayed Enhancement MR Imaging" by D. C. Peters et al., Radiology, Volume 243, 2007, page 690-695, that so-called delayed enhancement recording technology should be used to show up scars resulting from high-frequency ablation of the right atrium. It is proposed here that the proportion of the periphery of the atrium ablated should be determined as an assessment variable.

The delayed enhancement imaging method is described in more detail by U.S. Pat. No. 6,205,349 B1. After a magnetic resonance contrast agent has been administered here, there is a delay for a predetermined time period before T2-weighted magnetic resonance image data is recorded, in which damaged myocardial tissue can be clearly distinguished from normal myocardial tissue.

In a different approach US 2010/0160765 A1 and US 2010/0160768 A1 describe a method for determining the likelihood or risk of recurrence. It is proposed here that a global parameter should be determined, for example the ratio of ablated surface to non-ablated surface or the ratio of diseased to healthy tissue, with an increased likelihood of recurrence being assumed when a limit value is exceeded.

When assessing a treatment and also for diagnostic approaches however the described methods fall short, as they only consider the ablated surface or distance on a periphery around the pulmonary veins globally. This does not exclude the possibility of still-functioning aberrant conduction paths being present, as a narrow strip is sufficient for these. It should also be noted here that it is complex and generally barely possible for a diagnosing physician to make an image-based assessment, as possible conduction paths are very difficult to identify in the reconstructed slice images.

US 2008/0077032 A1 relates to methods, which provide diagnostic information and use endocardial surface data of a heart of a patient. In this process a model of the endocardial surface is used to determine measurements which have diagnostic relevance, for example the three-dimensional partial shortening of the left ventricle. Other examples allow characteristic variables of heart movement to be determined from heartbeats. It is also discussed in conjunction with pacemakers that the electrical progression of signals can be modeled, by applying an initial stimulus at a specified location of a network model.

An article by Olaf Dossel et al., "A Framework for Personalization of Computational Models of the Human Atria", $33^{rd}$ Annual International Conference of the IEEE EMBS, Boston, Massachusetts USA, 2011, page 4324-4328, relates to the step by step personalization of a calculation model for human atria. First CT or magnetic resonance data is used to create an anatomical model, over which a fiber structure is placed on the basis of a rule-based method. Late enhancement magnetic resonance imaging is proposed for displaying fibrotic tissue. Regions with a high signal level segmented there can be input into the geometric model of the atrium as additional labels.

SUMMARY OF INVENTION

The object of the application is to specify an improved method, which is suitable for assessing the presence of conduction paths in a chamber wall of the heart, such as of the atrium.

According to the application to achieve this object a method is proposed for determining electrical conduction path information in a chamber wall of a ventricle, such as of an atrium, of a patient, comprising the following automatically performed steps:

recording of a three-dimensional magnetic resonance image data set showing the ventricles, using a recording technology allowing the assignment of an electrical conductivity to a voxel based on image data of the magnetic resonance image dataset, segmenting of the chamber wall in the magnetic resonance image dataset, assigning a conductivity determined from the image data to sub-regions of the chamber wall corresponding to individual voxels of the magnetic resonance image dataset, creating a model of the chamber wall as a function of the conductivities and segmentation, determining the at least one conduction path information item describing an electrical conduction path running from at least one start point to at least one destination point through the chamber wall in the model.

As mentioned above, the method described here is suitable for an assessment of the success of the treatment to be performed after the treatment for a high-frequency ablation of an atrium as a ventricle of a patient. It is proposed here that the location and the spatial structure of the ventricle in question, such as of the atrium, should be determined from three-dimensional magnetic resonance data. The recording, for which either directly three-dimensional magnetic resonance imaging can be used or a stack of slice images can be produced, of the three-dimensional magnetic resonance data takes place in such a manner that the image data can be used to conclude the conductivity of the tissue in the voxels or other sub-regions of the chamber wall. Once both the location and geometry of the chamber wall and the electrical conductivity are known with local resolution, a model can be generated, in which the ability of the chamber wall to transport electrical signals can be assessed for specific conduction paths, it being possible here to utilize calculations, simulations and/or specific algorithms in order to determine conduction path information, which describes at least one electrical conduction path from a start point to a destination point. Start point and destination point are then selected appropriately, as will be examined below in detail, so that it is checked whether conduction from the point of origin of electrical signals, for example from ectopic foci, to muscle tissue is possible, where this would then be erroneously stimulated to produce movement.

In this manner the disclosed method firstly allows it to be checked specifically and with local resolution whether aberrant conduction paths are still present after therapeutic treatment and also, in a diagnostic application, fundamentally for the presence of such aberrant conduction paths to be checked. It is thus possible to estimate the risk of a recurrence or occurrence of atrial fibrillation or other disrupted rhythms, for example supraventricular tachycardia, more effectively than with known methods, which only specify the likelihood of recurrence or the like by estimating global parameters, so that narrow but relevant conduction paths can be overlooked.

A delayed enhancement technology is used here as the recording technology. Such a recording technology makes it possible to distinguish tissue types of different conductivity in chamber walls effectively. As mentioned above, the delayed enhancement method is described in more detail for example by U.S. Pat. No. 6,205,349 B1. As mentioned, a contrast agent is administered there, which accumulates over time in spaces between cells. This accumulation allows conclusions to be drawn about tissue properties, in this instance specifically conductivity. One feature of delayed enhancement recording technology is also that it is possible to distinguish the chamber wall clearly from other tissue types, so that segmentation remains possible.

In a further embodiment of the present application an inner and/or outer delimitation of the chamber wall and/or a locally resolved thickness of the chamber wall can be determined for the purpose of segmenting the chamber wall. Segmentation methods are already known in principle in the prior art. For example provision can be made here for the lumen of the ventricle, such as of the atrium, to be identified and delimited first here, with known segmentation algorithms being utilized. The result is a surface in the form of an inner delimitation of the ventricle. The outer delimitation of the ventricle can now also be determined by segmentation, so that a thickness of the chamber wall also necessarily results here.

In one embodiment of the present application the inner delimitation of the chamber wall is considered as an unrolled, two-dimensional surface as the basis for the model. If the inner delimitation of the ventricle, such as of the atrium, is known, it can be "unrolled" by corresponding deformation into a regular two-dimensional surface for the purpose of simpler further processing. The mapping rule for such a deformation can be stored, so that at the end of the disclosedly undertaken analysis the two-dimensional surface can be transferred back to the coordinate system of the three-dimensional magnetic resonance image dataset. It is further expedient here for surface elements of the surface to be considered and for a chamber wall thickness to be assigned to each considered surface element of the surface, as an absolute value and/or a voxel number. Provision can specifically be made for the surface to be subdivided into pixel-type surface elements, by laying a matrix or grid over the surface. By adding the depth information (thickness), provision can be made for voxel-type volume elements to be produced, the image data content of which can be determined by rebinning based on the voxels of the three-dimensional magnetic resonance image dataset. The magnetic resonance image data is reorganized into the sub-regions defined in the context of the model, such as into voxel-type volume elements, which extend according to the thickness of the chamber wall behind the pixel-type surface elements of the surface.

It should however be noted here that it is also conceivable to consider the inner delimitation of the chamber wall as a surface written into a volume, it being also possible here for the voxels of the magnetic resonance image dataset to be further evaluated as volume elements of said volume. If other volume elements are used here, a type of rebinning, or a reorganization, may be necessary here too.

In both the instances mentioned here in an embodiment of the present application in order to determine conductivity the image data for different considered surface elements of the inner delimitation of the chamber wall is integrated by way of the thickness of the chamber wall and the electrical conductivities are assigned from the integral values thus obtained, based on assignment information, such as a characteristic line and/or a limit value. Allocation of the electrical conductivity (it being possible for any scalar variable describing electrical conductivity to be used here) takes place based on the signal strength in the magnetic resonance image dataset, such as the delayed enhancement image, based on integration by way of the thickness of the chamber wall, in other words the edge diameter. In this embodiment so-called transmurality is also taken into account in the allocation of conductivity. Different assignment information is possible here, with a characteristic line based on calibration measurements and/or calculations and/or simulations. However a linear relationship as a function of signal intensity can also be used, with a binary allocation also being conceivable, when an integral value is below or above a threshold value.

It should however be noted that it is alternatively also possible to operate directly on the basis of the segmentation result. Thus it is conceivable for a conductivity derived from the image data to be assigned to each voxel of the chamber wall based on assignment information, such as a characteristic line and/or a limit value. The basis for the model is then an abstract quantity of voxels of the magnetic resonance image dataset, which have been identified as associated with the chamber wall. It is then expedient to allocate the conductivity value to these voxels as a function of their corresponding image data using a characteristic line.

According to the application however mapping takes place onto a two-dimensional model, using integral values for allocation, as the overall problem can then be considered two-dimensionally, in a two-dimensional matrix, which considerably simplifies calculations.

As mentioned above, it is conceivable for conductivity to be assigned to the sub-regions in the form of a binary value. A simple model results, which shows whether or not a considered sub-region of the chamber wall is conductive.

Specifically in this context, but also quite generally, it is then possible to use a path-finding algorithm to determine the conduction path information. Such path-finding algorithms are already known in principle and are for example also known from applications in motor vehicles, when conductivity is no longer considered in a binary manner. As it is possible there to find paths with the lowest possible consumption for example, it is conceivable in the disclosed method to use such algorithms to find conduction paths with the greatest possible conductivity, with low resistance, between start and destination points.

However it is alternatively or additionally also possible for a simulation to be performed to determine conduction path information, with a potential being applied between start point and destination point. For example the propagation of an electrical pulse from the start point, for example the pulmonary veins, can be simulated. This can be done for example by simulating an electrical potential from the start point to the destination point and determining the electric current for all possible propagation paths based on conductivity. Suitable simulation environments are already known in the prior art and can also take further effects into account.

It should generally be noted here that a number of start points can also form a cohesive start region and a number of destination points can form a cohesive destination region, with spatially separated start and destination points or regions being able to be treated by applying the potential between all start and destination points but also by considering the combinations individually. It is of course also possible when using algorithms, such as path-finding algorithms, to consider start regions made up of a number of start points, with the number of accessible paths overall increasing.

The edge of the entry region of a pulmonary vein and/or a lesion can expediently be selected as a start point. As experience with corresponding diseases, such as atrial fibrillation, shows, the entry regions of the pulmonary veins frequently form an exit point for electrical signals, which pass by way of aberrant conduction paths to muscle tissue. However lesions can also be a source of undesirably transmitted electrical signals. A transition to muscle tissue can expediently be selected as a destination point. When an electrical signal transmitted by way of an aberrant conduction path reaches muscle tissue, unwanted muscle stimulation can occur, so such destination points are appropriate.

In a further embodiment of the disclosed method a course and/or the resistance of at least one conduction path of lowest resistance can be determined as conduction path information.

It is conceivable for example to output the resistance of at least one conduction path of lowest resistance as a type of score, so that it can be concluded whether there is still a risk of erroneous transmission of electrical signals. If there are a number of spatially separated start points or destination points present, which do not form a cohesive start region or destination region, a specific assessment based on the conduction path of lowest resistance can be performed for each combination of such spatially separated points. However the course of at least one conduction paths of lowest resistance is also determined, so that a graphic display is also possible, showing the location of problematic conduction paths. All conduction paths below a specific resistance limit value can be shown here or a certain number of conduction paths of lowest resistance.

In a further embodiment of the present application provision can be made for the conduction paths of lowest resistance to be shown in a display of the image dataset and/or the chamber and/or the inner delimitation of the chamber. According to the application, a pictorial display of the determined conduction paths of lowest resistance can be provided, so that the determined conduction path information can be given even more clearly and comprehensibly. The conduction paths can be inserted into a display of the magnetic resonance image dataset, with a useful display also resulting if the inner delimitation of the chamber is displayed, as mentioned above, as a two-dimensional surface.

In addition to the method the application also relates to a magnetic resonance facility, comprising a control facility configured to perform a disclosed method. All the embodiments relating to the disclosed method can be applied in a similar manner to the disclosed magnetic resonance facility, so that the features of the present application can also be achieved here.

A magnetic resonance facility, as known in principle in the prior art, can be configured directly to perform the disclosed method by configuring a control facility accordingly. Software and hardware components, which implement the algorithms used in the context of the disclosed method, can be used for this purpose. It should be noted here that it is of course also possible to execute the disclosed method on another computation facility, for example an analysis facility or the like. Environments are known for example, in which data to be analyzed is transferred to an analysis server, which performs more computation-intensive analysis steps. The disclosed method can also be implemented on such an analysis server.

BRIEF DESCRIPTION OF THE DRAWINGS

Further features and details of the present application will emerge from the embodiments described in the following and from the drawing, in which.

DETAILED DESCRIPTION OF INVENTION

Figure 1:
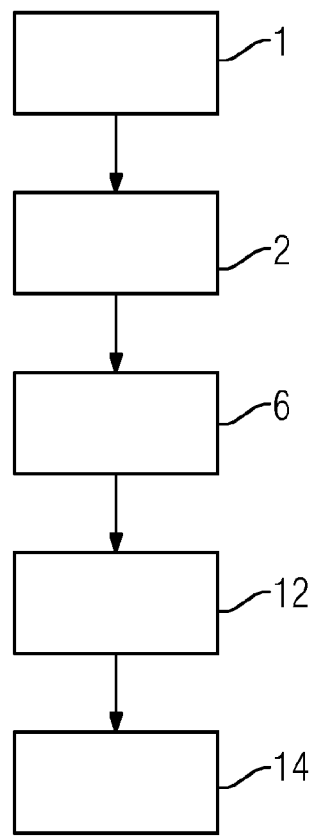
FIG. 1 shows a flow diagram of an embodiment of the disclosed method.

FIG. 1 shows a flow diagram of an embodiment of the disclosed method. The disclosed method is intended to allow aberrant conduction paths, which conduct electrical signals that occur as disruptive signals or circulate to the muscle tissue in the heart, to be detected more effectively.

To this end in a step 1 provision is first made for the recording of a three-dimensional magnetic resonance image dataset of the ventricle. The recording technology used here is a delayed enhancement technology, in other words after a contrast agent has been administered there is a delay of a certain time period until the contrast agent has accumulated in the tissue, specifically in the spaces between cells, so that it is easier to distinguish different types of tissue in respect of their electrical conductivity. This means that information about the tissue in respect of electrical conductivity can be obtained from the magnetic resonance signal.

The embodiment illustrated here relates to aberrant conduction paths in the atrium occurring in the context of atrial fibrillation, the left atrium being considered in more detail in the present instance. In step 2 the chamber wall of the left atrium is segmented in the magnetic resonance image dataset, see FIG. 2, in which the chamber wall 3 of the left atrium of the heart 4 is shown highlighted. For the purpose of segmentation provision is now first made for starting from the lumen 5 of the left atrium, to determine the inner delimitation of the chamber wall 3. Since it is also possible on the outside to distinguish the tissue of the chamber wall clearly from the surrounding types of tissue, a similar segmentation is also possible here, giving the outer delimitation of the chamber wall 3. All the voxels of the magnetic resonance image dataset located between the inner delimitation and the outer delimitation belong to the chamber wall and are marked correspondingly. The distance between the inner and outer delimitations gives the thickness of the chamber wall 3.

Based on the segmentation that takes place in step 2 a model of the chamber wall is now to be created, in which different sub-regions of the chamber wall, which will be examined in more detail below, are assigned conductivities. This takes place in a step 6 (FIG. 1). While it is in principle conceivable for the voxels marked as associated with the chamber wall 3 themselves to form the basis for the model, by deriving a conductivity as the conductivity value for a voxel from the corresponding image data of each voxel based on a characteristic line or other assignment information, which is possible due to the known relationship when recording using the delayed enhancement technology procedure is to be set out here.

Figure 3:
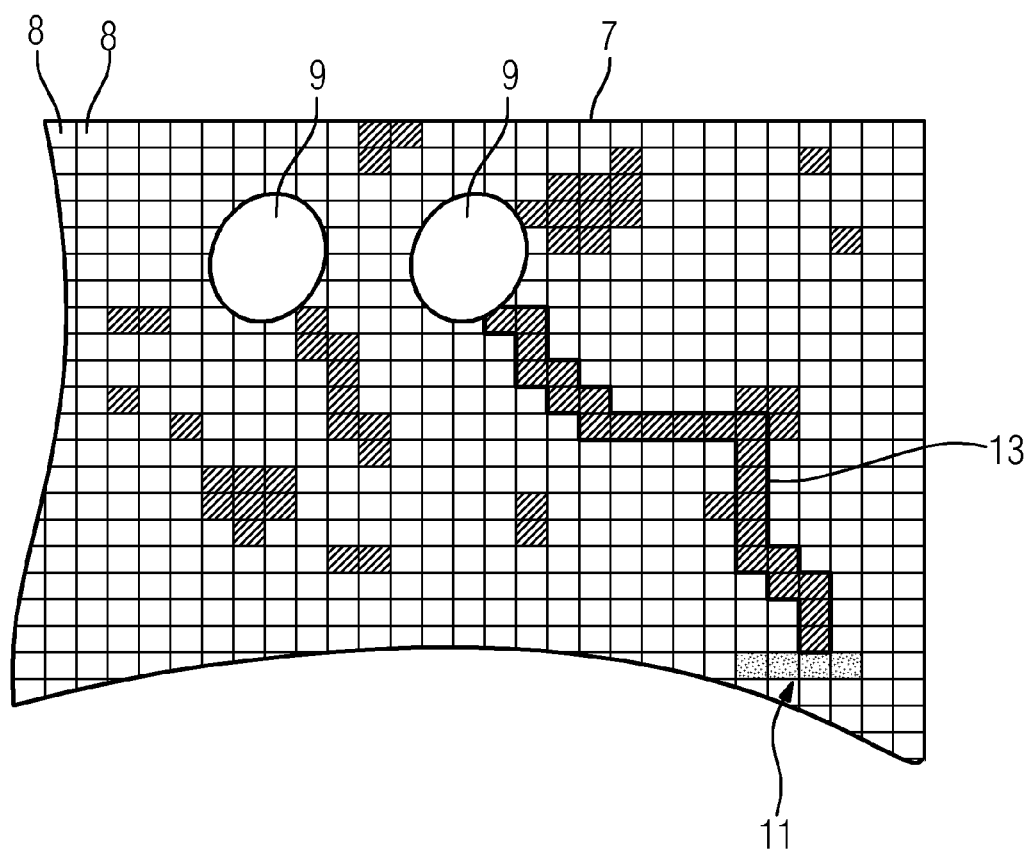
FIG. 3 shows a basic outline for allocating conductivities.

With this provision is first made to map the inner delimitation of the chamber wall 3, as segmented, onto a two-dimensional surface 7, as shown schematically in FIG. 3. The corresponding transformation rule is available here in the context of the disclosed method. The surface 7 is considered as a matrix, in other words the notional superimposition of a grid defines pixel-type surface elements 8 of the surface 7. The thickness of the chamber wall 3 to the outer delimitation is assigned to each of said surface elements 8, with voxel-type volume elements being present behind the surface elements 8 in the present instance, being filled with the correspondingly reorganized magnetic resonance image data. The magnetic resonance image data is now integrated along the thickness of the chamber wall 3, in other words the voxel-type volume elements present "behind" the surface elements 8, so that an integral value results for each surface element 8 of the surface 7.

It should however be noted here that the considerations applied here can also be performed three-dimensionally in the model illustrated by FIG. 3, with the transmurality in this embodiment being intended to be taken into account by way of the integration.

A conduction value is now assigned to the corresponding integral value for each surface element 8 based on the known properties of the delayed enhancement magnetic resonance technology, by a characteristic line. However just for clarity in this embodiment a simplified variant of the disclosed method is shown, in which the property "conducting" or "non-conducting" is simply assigned to each surface element 8 based on a threshold value, so that a binary classification results. Conducting surface elements 8 are shown hatched in FIG. 3. Non-conducting surface elements 8 are empty.

Figure 2:
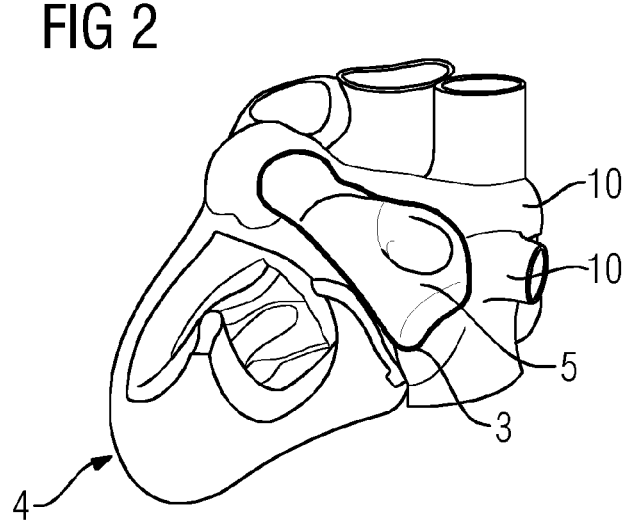
FIG. 2 shows a schematic diagram of a heart and the chamber wall of the left atrium.

Also shown schematically in FIG. 3 are entry regions 9 of the pulmonary veins 10 (see FIG. 2). As disrupting electrical signals generally start at the edge of the entry regions 9, in the present instance the surface elements 8 at the edges of the entry regions 9 form start points for the following consideration. The question now is whether there are aberrant conduction paths in the conductivity model, which allow the transmission of the electrical signals from the start points, here the edges of the entry regions 9, to destination points, with a destination region 11 formed from a number of destination points being shown dotted by way of example in FIG. 3. A transition to muscle tissue is present there.

In the embodiment illustrated here a path-finding algorithm is now used, step 12 in FIG. 1, to find a conduction path of lowest resistance from a start point to a destination point. Such a conduction path 13 is highlighted in FIG. 3. Path-finding algorithms are known in principle in the prior art and do not have to be looked at more closely here. Even in the more general instance, when for example there is a continuous assignment of electrical conductivity values to surface elements 8, cost-optimizing path-finding algorithms are already known, which can also be utilized in the disclosed method.

If there are a number of spatially separated start points or cohesive start regions formed from start points or spatially separated destination points/destination regions 11 present, conduction paths 13 of lowest resistance can of course also be calculated for different combinations; it is also conceivable to find a number of conduction paths 13 with the lowest resistances.

Figure 4:
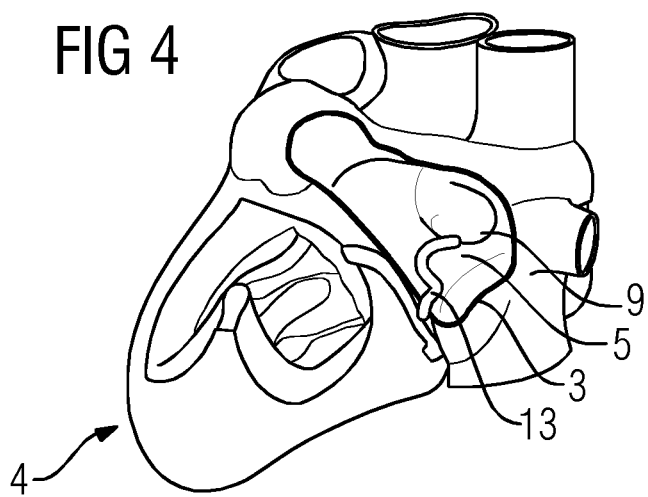
FIG. 4 shows a possible diagram of a conduction path of lowest resistance.

In a step 14, FIG. 1, the results are now displayed. The lowest resistance here can be shown itself as a sort of score but it is for a pictorial display to be shown. Once the transformation rule for determining the surface 7 has been stored, the conduction path 13 found can also be calculated back to the three-dimensional image dataset, so that a display, as shown by way of example in FIG. 4, results. This again shows the heart 4, with the conduction path 13 in the left atrium 5 on its chamber wall 3 highlighted clearly in color, as it leaves the entry region 9.

However other display options are also possible, for example with the conduction path 13 highlighted on a display of the surface 7, as in FIG. 3.

It should finally be noted here that it is conceivable, also with three-dimensional model considerations of electrical conductivity, instead of calculations, which operate for example by way of the path-finding algorithm, to perform simulations, in which a potential is applied between start and destination points and it is observed whether current paths develop.

Figure 5:
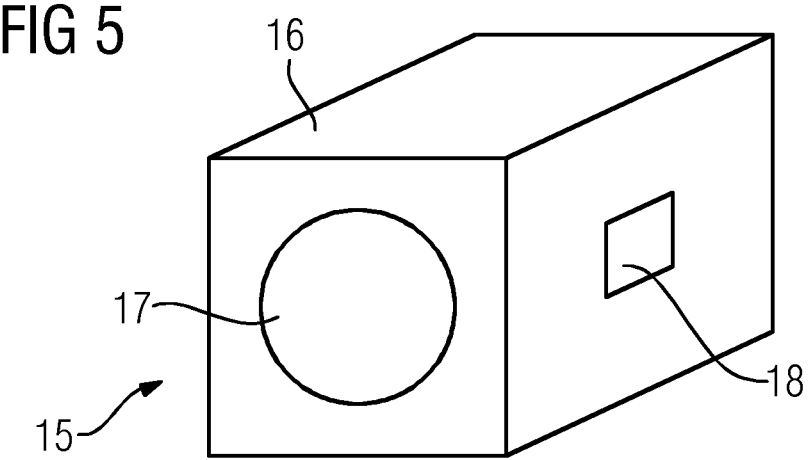
FIG. 5 shows a disclosed magnetic resonance facility.

Finally FIG. 5 shows a basic outline of a disclosed magnetic resonance facility 15, which in the usual manner comprises a main magnet unit 16 with a patient accommodation region 17, around which a high-frequency coil arrangement and a gradient coil arrangement for example can be disposed. The embodiments of such magnetic resonance facilities 15 are widely known in the prior art. The magnetic resonance facility 15 also comprises a control facility 18, which is configured to perform the disclosed method, so that the magnetic resonance image data recorded using the delayed enhancement technology can be analyzed immediately in situ in respect of conduction path information.

Although the application has been illustrated and described in greater detail using the embodiment, the application is not restricted by the disclosed examples and other variations can be derived therefrom by the person skilled in the art without departing from the scope of protection of the application.

The invention claimed is:

1. A method for determining an electrical conduction path information in a chamber wall of a ventricle of a patient, comprising:
   recording a three-dimensional magnetic resonance image dataset showing the ventricle using a delayed enhancement recording technology;
   segmenting the chamber wall in the magnetic resonance image dataset;
   determining an electrical conductivity based on image data of the magnetic resonance image dataset;
   assigning the electrical conductivity to sub-regions of the chamber wall corresponding to individual voxels of the magnetic resonance image dataset;
   creating a model of the chamber wall based on the electrical conductivity and the segmentation;
   determining the electrical conduction path information in the model describing an electrical conduction path running from a start point to a destination point through the chamber wall;
   displaying the electrical conduction path information; and
   checking whether an aberrant conduction path presents after therapeutic treatment of the patient based on the determined electrical conduction path information,
   wherein the assigning step further comprises:
      determining a locally resolved thickness of the chamber wall based on the segmentation;
      integrating the image data of the sub-regions along the thickness of the chamber wall; and
      assigning the electrical conductivity according to the integral value to the sub-regions of the chamber wall.

2. The method as claimed in claim 1, further comprising determining an inner and/or outer delimitation of the chamber wall on the segmentation.

3. The method as claimed in claim 2, wherein the model is created based on an unrolled and two-dimensional surface using the inner delimitation of the chamber wall.

4. The method as claimed in claim 3, wherein the thickness of the chamber wall is assigned to a surface element of the surface as an absolute value and/or a voxel number.

5. The method as claimed in claim 1, wherein the electrical conductivity is assigned to each voxel of the chamber wall based on an assignment information comprising a characteristic line and/or a limit value.

6. The method as claimed in claim 1, wherein the electrical conductivity is assigned to the sub-regions with a binary value.

7. The method as claimed in claim 1, wherein the electrical conduction path information is determined by a path-finding algorithm.

8. The method as claimed in claim 1, wherein the electrical conduction path information is determined by a simulation with a potential applied between the start point and the destination point.

9. The method as claimed in claim 1, wherein the start point is an edge of an entry region of a pulmonary vein and/or a lesion.

10. The method as claimed in claim 1, wherein the destination point is a transition to muscle tissue.

11. The method as claimed in claim 1, wherein the electrical conduction path information comprises a course and/or a resistance of an electrical conduction path of lowest resistance.

12. The method as claimed in claim 11, wherein the electrical conduction path of lowest resistance is shown in the three-dimensional magnetic resonance image dataset and/or in the ventricle and/or in an inner delimitation of the ventricle.

13. The method as claimed in claim 1, wherein the method steps are performed on an atrium of the patient.

* * * * *